United States Patent [19]  
Cardinal et al.

[11] Patent Number: 4,895,724  
[45] Date of Patent: Jan. 23, 1990

[54] CHITOSAN COMPOSITIONS FOR CONTROLLED AND PROLONGED RELEASE OF MACROMOLECULES

[75] Inventors: John R. Cardinal; William J. Curatolo, both of Old Lyme, Conn.; Charles D. Ebert, Brewster, N.Y.

[73] Assignee: Pfizer Inc., New York, N.Y.

[21] Appl. No.: 742,500

[22] Filed: Jun. 7, 1985

[51] Int. Cl.$^4$ .......................... A61K 9/62; A61K 9/52; A61K 37/00

[52] U.S. Cl. ................... 424/418; 424/422; 424/451; 424/460; 424/461; 424/457; 424/484; 424/488; 424/489; 424/493; 424/499; 424/88; 424/85.4; 424/94.1; 514/2; 514/21; 514/8; 514/23; 514/54; 514/55; 514/964; 514/965; 604/890.1; 604/891.1

[58] Field of Search ............... 424/418, 422, 451, 457, 424/461, 484, 488–489, 493, 499, 88, 94.1; 604/890.1, 891.1; 514/2, 8, 21, 23, 54

[56] References Cited

U.S. PATENT DOCUMENTS

| | | | |
|---|---|---|---|
| 4,164,560 | 8/1979 | Folkman et al. | 424/78 |
| 4,351,337 | 9/1982 | Sidman | 604/891 |
| 4,536,387 | 8/1985 | Sakamato et al. | 514/774 |
| 4,638,045 | 1/1987 | Kohn et al. | 604/891 |
| 4,668,506 | 5/1987 | Bawa | 604/894 |
| 4,675,381 | 6/1987 | Bichon | 604/890 |
| 4,690,822 | 9/1987 | Uemura et al. | 424/488 |
| 4,704,268 | 11/1987 | Kifune | 424/489 |
| 4,808,707 | 2/1989 | Daly et al. | 424/461 |

FOREIGN PATENT DOCUMENTS

| | | |
|---|---|---|
| 8767199 | 7/1987 | Australia . |
| 0092918 | 11/1913 | European Pat. Off. . |
| 7134412 | 8/1982 | Japan . |
| 1197529 | 9/1986 | Japan . |
| 2083884 | 4/1987 | Japan . |

OTHER PUBLICATIONS

Miyazaki et al., Chem. Pharm. Bull., 29 (10), 3067–3069, (1981).

Sawayanagi et al., Chem. Pharm. Bull., 39 (11), 4213–4215 (1982).

*Primary Examiner*—Garnette D. Draper  
*Attorney, Agent, or Firm*—Peter C. Richardson; Paul H. Ginsburg; Gezina Holtrust

[57] ABSTRACT

Compositions for the controlled and prolonged release of macromolecular compounds comprise a porous matrix of chitosan having dispersed therein the macromolecular compound. Examples of macromolecules used in the composition are pharmacologically active ones such as peptide hormones, e.g. growth hormone.

20 Claims, No Drawings

CHITOSAN COMPOSITIONS FOR CONTROLLED AND PROLONGED RELEASE OF MACROMOLECULES

BACKGROUND OF THE INVENTION

The invention relates to compositions for controlled and prolonged release of macromolecules, particularly those having pharmacological usefulness, from a porous matrix of chitosan.

Controlled and prolonged release of pharmacologically active (hereafter "pharmacological") compounds is known in the art and described in many patents. Most of these patents, however, deal with release of low molecular weight compounds. Release of macromolecular compounds has been problematic due to difficulties inherent in such release. Thus, macromolecular compounds do not diffuse as easily through the matrix in which they are contained and they tend to be susceptible to deactivation during preparation of the delivery device and during release from the device, e.g. polypeptides and proteins are denatured.

U.S. Pat. No. 4,164,560 describes release of a macromolecular drug from a matrix of biocompatible polymer that remains substantially intact throughout the release of the drug. European Pat. Publication No. 92,918 discloses sustained release of pharmacologically active polypeptides copolymer having a hydrophobic and hydrophilic component. Neither reference includes chitosan as a possible matrix.

Miyazaki et al., Chem. Pharm. Bull. 29 (10), 3067-3069 (1981) suggest chitin and chitosan for sustained release of drugs. However, only the low molecular weight drugs indomethacin and papaverine hydrochloride are mentioned. Macromolecular drugs are clearly not considered. Similarly Sawayanagi et al., Chem Pharm. Bull., 39 (11), 4213-4215 (1982) describe sustained release of a low molecular weight drug, propranolol hydrochloride, from chitosan.

SUMMARY OF THE INVENTION

According to the invention, a composition for controlled and prolonged release of at least one macromolecular compound is provided, said composition comprising a porous matrix of chitosan having dispersed therein said macromolecular compound.

The invention also provides a method of administering a pharmacological macromolecular compound by injecting or implanting in a subject in need of treatment a porous chitosan matrix having dispersed therein said macromolecular compound.

DETAILED DESCRIPTION OF THE INVENTION

The compositions of the invention are particularly useful when injected or implanted in living tissue for slow and prolonged release of pharmacological macromolecular compounds. The continued release of drugs over a long time period following a single administration has significant practical advantages. However, the composition may also be used in extracorporeal applications such, as medical instruments, e.g. kidney dialysis machines. In such instruments, release of macromolecular compounds may be advantageous, e.g. release of heparin into blood during kidney dialysis.

This invention is applicable to any macromolecular compound in general and pharmacological macromolecular compounds in particular. For the purposes of this invention, macromolecules have a molecular weight of at least 1000. The macromolecular pharmacological compounds of the invention are pharmacologically active in warm blooded animals including humans, and farm animals, or they are present, in compositions having pharmacological activity, e.g. for kidney dialysis.

Examples of macromolecular pharmacological compounds of use in the invention are proteins and polypeptides The proteins include peptide hormones such as growth hormone e.g. bovine growth hormone, insulin, thyroid stimulating hormone, follicle stimulating hormone, luteinising hormone, chorionic gonadotropin, vasopressin, adrenocorticotropic hormone, thyroid stimulating hormone; oxytocin; interferon; gastrin; secretin; calcitonin; endorphins; angiotensins, renin, bradykinin; and somatomedins. Other macromolecules include enzymes such as hydrolases, lysases, isomerases, proteases, ligases, phosphatases and peptidases; and polysaccharides such as heparin and dextran. An example of a macromolecular pharmacological compound which may be present in compositions having pharmacological activity is albumin. Yet other macromolecules are antigenic materials derived from infectious agents such as viruses to provide immunoprotection against such agent.

The amount of macromolecular compound present in the composition of the invention ranges from about 5 to 50%, preferably 30 to 50% by weight. The amount of macromolecular compound depends on the particular use of such compound. In the case of a pharmacological macromolecular compound such as a hormone, the amount is in any event larger than a standard single dosage, and depends on the time of treatment, the daily dosage and the in vivo release rate from the chitosan matrix. For example, bovine growth hormone may be administered to cows at a daily dosage of 40 mg to increase milk production. If a ten day treatment is desired, the chitosan matrix must contain at least 400 mg bovine growth hormone and must release the hormone at about 40 mg per day. Also, the daily dosage may be made to release either at a constant rate or at a variable rate over the total time of treatment. For instance, a large initial dosage may be followed by a constant or a steadily decreasing dosage.

Chitosan is a common name for the deacetylated form of chitin. Chitin is a natural product comprising poly(N-acetyl-D-glucosamine). On deacetylation, chitin becomes soluble in dilute organic acid. Solubilization generally begins at about 60%, usually about 75%, deacetylation depending on the molecular weight of the chitosan formed. The molecular weight of chitosan typically ranges from about 50,000 to 4 million. The chitosan of use in the invention is 70-78% preferably about 90 to 95% deacetylated and has a viscosity average molecular weight of about 100,000 to two million.

Preferably, the chitosan used is in relatively pure form. Methods for the manufacture of pure chitosan are known. Generally, chitin is milled into a powder and demineralized with an organic acid such as acetic acid. Proteins and lipids are then removed by treatment with a base such as sodium hydroxide, followed by chitin deacetylation by treatment with concentrated base such as 80% sodium hydroxide. The chitosan formed is washed with water until a neutral pH is reached.

Chitosan is biocompatible with living tissue such that there is substantially no adverse tissue reaction on chitosan injection or implantation in living tissue.

It is understood that the porous matrix of chitosan is a chitosan polymer network containing contiguous channels throughout said network. The macromolecular compound is dispersed in these contiguous channels. The rate of release of the macromolecular compound depends on the diameter of the channels. Control of the channel diameter and thus the release rate may be by cross-linking and other methods described below.

In one method of preparing the porous chitosan matrix, chitosan is first dissolved in any one of a large number of solvents. Solvents for chitosan include for example mineral acids such as hydrochloric acid and nitric acid, and organic acids such as formic, acetic, citric, pyruvic, lactic, glycolic, maleic, malic, malonic, tartaric, dichloroacetic and oxalic acid. Preferably, the solvent is acetic acid resulting in formation of chitosan acetate. Other acid solvents form different chitosan salts having varying physical properties. Films are cast from the solution of the chitosan. After drying, the films are milled to form small particles.

In another method, an acidic solution of chitosan is added dropwise to a basic solution which precipitates generally spherical chitosan beads.

In a third method, an acidic solution of chitosan is vigorously stirred in a large volume of non-polar liquid such as mineral oil or hexane. Small droplets of emulsified chitosan are formed. The size of the droplets may be controlled by controlling the process conditions such as stirring speed, viscosity of the chitosan solution and addition of emulsifying agents.

Chitosan particles e.g. beads may also be formed on spray-drying an acidic solution of chitosan.

The macromolecular compound is incorporated in the chitosan matrix during any step of the above described procedures. Thus, the macromolecular compound may be added before or after casting or before or after grinding the chitosan film formed in the first method described above. Conveniently, the macromolecular compound is dissolved together with the chitosan in the solvent for chitosan in any one of the described methods. If added after the chitosan is formed into a film, beads or particles, a concentrated aqueous solution of the macromolecular compound is contacted with such film, beads or particles to allow for diffusion of the compound into the chitosan matrix.

For the purpose of this invention, a chitosan matrix includes a matrix of chitosan itself, a matrix of chitosan salts of the above mentioned acids or, a matrix of a mixture of chitosan and said chitosan salts.

When in the disclosure below, reference is made to chitosan films, such disclosure equally applies to chitosan particles.

The suitability of a method for preparing a chitosan matrix depends on the particular macromolecule dispersed in the matrix. Each macromolecule, e.g. a protein, has a different sensitivity to process conditions such as heat and pH. The process conditions for making the compositions of the invention must be chosen to maximize stabilization of the incorporated protein. Such process conditions include the nature of the chitosan solvent, the temperature and duration of the film drying step, and the presence of protein stabilizers. Many protein stabilizers are described in the prior art, including inorganic salts, particularly calcium and ammonium salts, sugars, polyols and albumin. Generally, a temperature lower than room temperature is preferred since proteins tend to denature less at lower temperature. However, it is known that different proteins denature at different temperatures. It is also known that the denaturation temperature depends on the pH. Some proteins are stable at acidic pH, others at basic pH. To establish the best process temperature and pH, the protein should be treated at different temperatures and pH's to determine whether denaturation occurs or not. It should also be determined whether a particular protein renatures on cooling and whether any such renaturation is partial or not. In general, a neutral pH is best and a pH of higher than 10 or less than 3 should be avoided. Drying of the formed chitosan matrix is generally at low temperature, usually room temperature. The duration of drying may be shortened by applying a vacuum during the drying. Exposure of proteins to severe conditions may be avoided by diffusing the protein into the chitosan matrix after formation thereof as described above.

After formation of the chitosan matrix by any one of the above methods, treatment with an organic solvent or a base may follow to modify the physical properties of the chitosan matrix, particularly the solubility thereof in aqueous solvents and the release properties on use.

The treatment is by contacting the matrix with the organic solvent or the base, e.g. by immersing or soaking of the chitosan film or beads in the solvent or base.

The length of such treatment affects the release rate of the matrix. The longer the treatment, the longer the time of release of the macromolecule dispersed in the matrix. In turn, the length of treatment depends on the solvent or base used and the temperature of the treatment. In general, the higher the temperature, the shorter the treatment required to decrease the release rate. When the macromolecular compound is a protein, generally low temperatures should be used to avoid denaturation, as discussed above, with accordingly longer treatment times.

For the treatment with a base, a wide variety of bases may be used including but not limited to alkali metal hydroxides such as sodium and potassium hydroxide, ammonium hydroxide, and alkyl amines such as triethylamine. The treatment with a base may be disadvantageous when using a protein or polypeptide macromolecule since denaturation may occur at high pH. The base treatment may be useful for polysaccharide macromolecules such as heparin and dextran which are relatively insensitive to pH changes.

The treatment with an organic solvent is with common organic solvents such as methanol, ethanol, isopropanol, acetone, or dimethylsulfoxide. Mixtures of solvents may be used. For instance, treatment with methanol is for relatively short periods of time ranging from ten minutes to a few hours (e.g. 3-5 hours. Such treatment may be extended and therefore easier to control by adding ethanol. Mixtures of methanol and ethanol in a weight ratio of 50:50 may be used.

According to an aspect of the invention, the chitosan may be cross-linked either before or after loading of the matrix with the macromolecule. Cross-linking agents of use before loading are small sized ones such as glutaraldehyde, glyoxal, epichlorohydrin, succinaldehyde, 1,10-decanedial, trichlorotriazine, benzoquinone, and bisepoxiranes. They are capable of penetrating the pores of the matrix and affecting the release rate. Thus, the macromolecule release rate is proportional to the extent of the cross-linking in that the more cross-linking takes place the lower the rate of release of the macromolecule.

The cross-linking is by contacting a solution of the cross-linking agent, e.g. glutaraldehyde in methanol, with a chitosan matrix. The higher the concentration of the agent, the slower the release, and the longer the treatment, the slower the release.

Cross-linking agents of use in surface crosslinking a loaded chitosan matrix are macromolecular compounds having more than one aldehyde group. Such polyaldehydes are generally not capable of penetrating the chitosan matrix and affecting the macromolecule in the matrix. Any high molecular weight polysaccharide polyaldehyde may be used. Examples of useful polysaccharides are dextran, gum arabic, gum karya, pectin, carrageenan, alginic acid, and starch. Specific examples of high molecular weight cross-linking agents are oxidized polysaccharides such as dextran dialdehyde and starch dialdehyde, and dialdehydes of carageenan or alginic acid. Synthetic polyaldehydes such as polyacrylic acid reduced to the aldehyde may be used as well.

The following examples illustrate the invention.

EXAMPLE 1

Crab shell chitin was milled to a powder (200 g), and was demineralized by twice contacting with 1M acetic acid (2 liter) at room temperature for 24 hours. Protein and lipid contaminants were removed by three times soaking with 2 liters of 0.5 M NaOH at 50° C. for 1 hour yielding 160 g purified chitin. The chitin (100 g) was deacetylated by three times contacting with 1.5 liter of 80% NaOH in water at 110° C. for 1 hour. Between base treatments, the chitin/chitosan was washed extensively with water. The resulting chitosan was dissolved in 0.1 M acetic acid (100 ml per gram chitosan), filtered, and precipitated as thin threads in a large excess of 0.5 M NaOH. The thin chitosan threads were further deacetylated by contacting with 80% NaOH at 110° C. for two hours. This material was washed until a neutral pH was reached, and dried. Yield: 60 g. The chitosan was prepared by this method is about 90–95% deacetylated, and has a viscosity average molecular weight of about 1–2 million.

EXAMPLE 2

Chitosan (0.9 g) prepared by the method of Example 1 and bovine serum albumin (BSA) (0.1 g) were dissolved in 50 ml 0.1 M acetic acid. This solution was poured into a crystallizing dish and was dried to a film in a convection oven at 23° C. for 17 hours. This film was divided into three pieces, which were incubated in methanol for 0, 10, or 60 minutes. The films were air dried and milled to form small particles which passed through a 40 mesh screen. The BSA content of these particles was 10 wt.%. 100 Mg of chitosan/BSA particles were placed in a vial containing 15 ml of a buffer consisting of 0.1M sodium phosphate (pH 7.4), 0.02% sodium azide, made up with sodium chloride to 289 mOsm/kg. The vial was gently tumbled at room temperature to provide mild but homogeneous mixing. At various times, an aliquot was removed from the incubation medium, and was replaced with an equivalent amount of buffer. The protein concentration in each aliquot was determined by a chemical assay.

The kinetics of BSA release are presented in Table I for chitosan/BSA particles derived from methanol-treated and untreated films. Chitosan/BSA particles which were not treated with methanol released most of their BSA within two days. This constitutes a controlled release of BSA, since BSA in the absence of chitosan dissolved in approximately one minute under the conditions of this example. Methanol-treated particles released their BSA at a much slower rate. The particles treated with methanol for 10 minutes released about 60% BSA gradually over 30 days and the particles treated with methanol for one hour released 40% BSA gradually over 30 days. The rate of BSA release thus can be controlled by controlling the duration of the methanol treatment.

TABLE I

| | Percent BSA Released | | |
|---|---|---|---|
| Release Time (days) | Untreated | Methanol Treated (10 minutes) | Methanol Treated (60 minutes) |
| 1 | 78.8 | 28.6 | 21.0 |
| 2 | 92.2 | 32.9 | 25.7 |
| 6 | 92.3 | 43.0 | 30.8 |
| 8 | 95.6 | 48.8 | 35.1 |
| 13 | 93.9 | 53.2 | 37.4 |
| 16 | 96.7 | 56.7 | 39.2 |
| 23 | 97.2 | 60.3 | 42.2 |
| 33 | 98.3 | 65.3 | 45.3 |

EXAMPLE 3

Chitosan/BSA films were prepared as in Example 2. The films were incubated in 1% methanolic sodium hydroxide for various time periods and milled to form particles. Chitosan/BSA particles which were incubated in methanolic base released BSA slower than particles which were treated with methanol alone. For example, chitosan/BSA particles which were incubated in methanol for 30 minutes released 66.1% of the BSA load in 23 days. Particles which were incubated in 1% methanolic sodium hydroxide for 30 minutes released 25.3% of the BSA load in 23 days. The time of incubation in 1% methanolic sodium hydroxide was varied from ten minutes to sixty minutes. Increase in incubation time resulted in a decrease in the ultimate BSA release rate. The sodium hydroxide concentration was also varied; decrease in sodium hydroxide concentration in the methanolic base treatment resulted in an increase in the ultimate BSA release rate.

A methanolic solution of the organic base triethylamine was also used instead of methanolic sodium hydroxide. Particles which were previously treated with 2% methanolic triethylamine released BSA more slowly than particles previously treated with methanol alone.

This example demonstrates that control over the BSA release rate can be exerted by treatment of chitosan/BSA films with base. The ultimate release rate can be varied by varying the base, the base concentration and the duration of the base treatment.

EXAMPLE 4

Chitosan films containing the protein alkaline phosphatase (AP) were prepared by the method in Example 2. The films were incubated in methanol for various time periods, and were milled to form particles. Chitosan/AP particles exhibited controlled release of AP under the experimental conditions of Example 2. Treatment with methanol resulted in slower AP release, which could be controlled by varying the duration of the methanol treatment. These compositions release enzymatically active AP as assayed by dephosphorylation of p-nitrophenylphosphate.

EXAMPLE 5

Chitosan (0.9 g) was dissolved in 40 ml 0.1M acetic acid. Bovine growth hormone (BGH) in an amount of 0.1 g was suspended in 10 ml 0.1 M acetic acid, mixed with the chitosan solution and poured onto a Teflon (registered Trade Mark) pan. After drying at room temperature for 17 hours in a laminar flow hood, a thin film was obtained. The film was divided in half. One half was soaked in methanol for one hour at 23° C., and dried. Each half of the film was milled and sieved through a 40 U.S. Standard Size mesh screen. The BGH content of the formed particles was 10 wt. %.

Under the controlled experimental conditions of Example 2, untreated chtosan/BGH particles released 85% of BGH over 2 days whereas the methanol-treated particles released 32% BGH in 2 days and 45% BGH in 20 days.

EXAMPLE 6

Chitosan/BSA films were prepared as in Example 2 at 10 wt. % BSA. One film was treated with methanol at 4° C. for one hour, a second film was treated with methanol at 23° C. for one hour, and a third film was not treated. The films were milled to form particles. The particles were tested for BSA release as in Example 2.

The untreated particles released 100% BSA in one day. At the end of one day, the particles treated at 4° C. had released 64% BSA and the particles treated at 23° C. had released 10% BSA.

This example demonstrates that the protein release rate can be varied by varying the temperature of the methanol treatment.

EXAMPLE 7

Chitosan (0.9 g) and BSA (0.4 g) were dissolved in 50 ml 0.1M acetic acid. The formed solution was poured onto a Teflon pan and dried at 23° C. in a hood for 17 hours. The resulting film was cut in half and one half was treated with methanol at 23° C. for one hour. The films were milled into particles and tested for BSA release as in Example 2. The BSA content of these particles was 31%.

The release of BSA from these particles was assayed as in Example 2. The untreated particles released 100% BSA within one day. The methanol-treated particles released 37% BSA in the first day and 43% BSA in the first 15 days.

The above demonstrates that the protein content can be increased while still achieving controlled protein release.

EXAMPLE 8

Chitosan (1.8 g) and BSA (0.2 g) were dissolved 80 ml 0.1 M acetic acid. The formed solution was poured onto a Teflon pan and dried at 23° C. for 17 hours in a hood. The resulting film was divided into pieces which were incubated for one hour in 50/50 ethanol/ methanol, 25/75 ethanol/methanol or methanol. The treated films were dried and milled into particles, and protein release was assayed as in Example 2. Particles treated with 50/50 ethanol/methanol released 58% of their protein in 25 days. Particles treated with 25/75 ethanol/methanol released 42% of their protein in 25 days. Particles treated with methanol released 12% of their protein in 25 days.

This test shows that the effect of methanol on protein release can be controlled by mixing methanol with other solvents.

EXAMPLE 9

A chitosan film containing 10 wt % BSA was prepared as in Example 2. The film was divided into two pieces, and one piece was incubated in methanol for one hour at room temperature and air dried. Discs of 1 cm diameter were cut from the untreated and methanol-treated films.

One hundred mg of chitosan/BSA discs were placed in a vial, and protein release was assayed as in Example 2. Untreated discs released 45% of their protein in ten days and 77% of their protein in forty days. Methanol-treated discs released 19% of their protein in ten days and 33% of their protein in forty days.

This test demonstrates controlled release of macromolecules from a chitosan-based implantable device.

EXAMPLE 10

Chitosan (2.7 g) was dissolved in 90 ml of 0.1M acetic acid. To this solution was added 300 mb BSA dissolved in 10 ml deionized water. The resulting solution was cast as a film on glass, dried, milled and sieved to provide a 40/100 mesh particle size range. The BSA content of these particles was 10 wt. %. BSA-loaded chitosan particles (0.2 g) were reacted with 0.1% glutaraldehyde or 0.2% glutaraldehyde in a 4/1 mixture of methanol/0.025M sodium phosphate (pH 8.0) for one minute at room temperature. A control sample was treated similarly in the absence of glutaraldehyde. The particles were collected on a fritted glass funnel, extensively washed with methanol and vacuum dried.

Release of BSA from these particles was assayed as in Example 2. Control particles (treated with 0% glutaraldehyde in methanol/buffer) released 25% and 35% of the loaded BSA in five days and twenty days, respectively. Particles treated with 0.1% glutaraldehyde released 11% and 18% of the loaded BSA in five days and twenty days, respectively. Particles treated with 0.2% glutaraldehyde released 7% and 13% of the loaded BSA in five days and twenty days, respectively.

This examples demonstrates that glutaraldehyde treatment can be used to decrease the BSA release rate and that controlled variation of the conditions of treatment can be used to control the BSA release rate.

EXAMPLE 11

Chitosan (3.6 g) was dissolved in 160 ml 0.1M mixed with the chitosan acetic acid. BGH (0.4 g) was solution, and the mixture was cast as a film on glass, dried, milled and sieved to provide a 40/100 mesh particle size range. The BGH content of these particles was 10 wt. %. The BGH-loaded chitosan particles (0.2 g) were reacted with 0% or 0.2% glutaraldehyde in a 4/1 mixture of methanol/0.025M sodium phosphate (pH 8.0) for one minute at room temperature. The particles were collected on a fritted glass funnel, extensively washed with methanol and vacuum dried.

Release of BGH from these particles was assayed as in Example 2. Control particles (treated with 0% glutaraldehyde in methanol/buffer) released 44% and 67% of the loaded BGH in ten days and forty days, respectively. Particles treated with 0.2% glutaraldehyde released 34% and 49% of the loaded BGH in ten days nd forty days, respectively. This example demonstrates that glutaraldehyde treatment can be used to decrease the BGH release rate.

We claim:

1. A composition for controlled and prolonged release of at least one macromoleculor compound which composition comprises a porous mix of chitosan having dispersed therein said macromolecular compound, and which composition has been contacted with at least one of an organic solvent or a base.

2. A composition according to claim 1 wherein said composition is injectable or implantable 3. A composition according to claim 1 wherein said macromolecular compound is pharmacologically active.

4. A composition according to claim 1 wherein said macromolecular compound is selected from the group consisting of proteins and polypeptide.

5. A composition according to claim 1 wherein said macromolecular compound is selected from the group consisting of hormones and enzymes.

6. A composition according to claim 5 wherein said hormone is bovine growth hormone.

7. A composition according to claim 1 wherein said macromolecular compound is an antigen of biological origin.

8. A composition according to claim 1 wherein said organic solvent is an alcohol.

9. A composition according to claim 1 wherein said organic solvent is methanol.

10. A composition according to claim 1 wherein said composition is in the form of particles.

11. A composition according to claim 1 wherein said macromolecular compound is present in an amount of 5 to 50 percent by weight.

12. A composition according to claim 1 wherein said chitosan is derived from chitin which has been about 90 to 90% deacetylated.

13. A composition according to claim 12 wherein said chitosan has a molecular weight ranging from 100,000 to two million.

14. A composition for controlled and prolonged release of a macromolecular compound which composition comprises a porous matrix of crosslinked chitosan having dispersed therein said macromolecular compound.

15. A composition according to claim 14 wherein said chitosan is cross-linked with a cross-linking agent selected from the group consisting of glutaraldehyde, glyoxal, epichlorohydrin, succinaldehyde, 1,10-decandeial, trichlorotriazine, benzoquinone, and bisepoxiranes.

16. A composition according to claim 14 wherein said chitosan is a cross-linked at the surface of said porous matrix.

17. A composition according to claim 16 wherein said surface cross-linking is with a macromolecular compound containing more than one aldehyde group.

18. A composition according to claim 17 wherein said macromolecular compound containing more than one aldehyde group is an oxidized polysaccharide.

19. A composition according to claim 18 wherein said oxidized polysaccharide is selected from the group consisting of starch dialdehyde and dextran dialdehyde.

20. A method of administering a pharmacologically active macromolecular compound which comprises injecting or implanting in a subject in need of treatment a porous chitosan matrix having said macromolecular compound dispersed therein.

* * * * *